United States Patent [19]
Sakota et al.

[11] Patent Number: 5,882,289
[45] Date of Patent: Mar. 16, 1999

[54] CENTRIFUGE BOWL WITH IMPROVED CORE STRUCTURE

[75] Inventors: Koichiro Sakota, Chofu; Toshiyasu Ohashi; Jun Tang, both of Tokyo, all of Japan

[73] Assignee: Haemonetics Corporation, Braintree, Mass.

[21] Appl. No.: 828,745

[22] Filed: Mar. 26, 1997

[30] Foreign Application Priority Data

Apr. 3, 1996 [JP] Japan .................................. 8-081362

[51] Int. Cl.⁶ ........................................................ B04B 7/12
[52] U.S. Cl. ................................................ 494/41; 494/67
[58] Field of Search .............................. 494/12, 38, 41, 494/43, 65, 67, 85

[56] References Cited

U.S. PATENT DOCUMENTS

| | | | |
|---|---|---|---|
| 3,409,213 | 11/1968 | Latham, Jr. ............................. | 494/41 |
| 3,565,330 | 2/1971 | Latham . | |
| 4,140,268 | 2/1979 | Lacour .................................... | 494/41 |
| 4,692,136 | 9/1987 | Feldman et al. ........................ | 494/38 |
| 4,859,333 | 8/1989 | Panzani .................................. | 494/38 |
| 4,879,031 | 11/1989 | Panzani .................................. | 494/38 |
| 4,943,273 | 7/1990 | Pages ..................................... | 494/41 |
| 4,983,158 | 1/1991 | Headley . | |
| 5,045,048 | 9/1991 | Kaleskas et al. . | |
| 5,100,372 | 3/1992 | Headley .................................. | 494/38 |
| 5,387,174 | 2/1995 | Rochat . | |
| 5,405,308 | 4/1995 | Headley et al. . | |
| 5,505,683 | 4/1996 | Geringer et al. ........................ | 494/41 |
| 5,514,070 | 5/1996 | Pages . | |
| 5,547,453 | 8/1996 | Di Perna . | |
| 5,551,941 | 9/1996 | Howell . | |
| 5,551,942 | 9/1996 | Brown et al. . | |

FOREIGN PATENT DOCUMENTS 59-69166   4/1984   Japan ..................................... 494/41

Primary Examiner—Charles E. Cooley
Attorney, Agent, or Firm—Cesari and McKenna, LLP

[57] ABSTRACT

A centrifuge bowl suitable for separating blood components, in particular concentrated red blood cells. A centrifuge bowl 10 comprises a core 14 having an annular portion 50A and a cylindrical outer wall 50. Annular portion 50A has a thick wall for minimizing the holdup volume of blood components within a collection chamber CC and the radially inner wall of the annular portion is disposed radially closely adjacent to the opening defined by skirts 24a, 25a. The outer wall 50 defines a separation chamber SC with bowl body 12 and its upper tapered portion defines a separation region S. Three slit-like openings 52 are formed at the junction between outer wall 50 and annular portion 50A, thereby prevent back flow while permitting flow of blood components from separation chamber SC to collection chamber CC. The upper end of outer wall 50 is formed with a cylindrical hub 50B extending toward the skirt member, which hub 50B serves to prevent fluid in collection chamber CC from flowing to the interior of bowl body 12 through central opening 56.

27 Claims, 10 Drawing Sheets

CENTRIFUGE BOWL WITH IMPROVED CORE STRUCTURE

TECHNICAL FIELD

The present invention relates to the field of blood processing, in particular to centrifuge bowls for separating blood components by centrifugation and cores therefor.

BACKGROUND ART

Whole human blood includes blood cells such as red blood cells, white blood cells and platelets and these cells are suspended in plasma, an aqueous solution of proteins and other chemicals. Blood transfusions used to be made using whole blood. Recently, however, blood transfusions are widely given by transfusing only those blood components required by a particular patient instead of using a transfusion of whole blood. Transfusing only those blood components necessary saves the available supply of blood, and in many cases, is convenient for the patient.

Centrifugation has been widely accepted as a technique for separating blood components such as plasma and platelets from whole blood, wherein blood components are separated depending upon their specific gravities. Disposable centrifuge rotors or bowls have been developed for separating blood components by such centrifugation and for washing blood cell components collected from a surgical site.

Typical examples include a centrifuge bowl of the type disclosed in U.S. Pat. No. 4,300,717 ("Latham" bowl) and a centrifuge bowl of the type disclosed in U.S. Pat. No. 4,086,924 ("Grenade" bowl). The bowl in each case comprises a rotor portion in which blood components are separated and a stator portion having an inlet port and an outlet port, and a rotary seal combines these portions together. Anticoagulated whole blood and/or wash solution is introduced to the interior of the rotor portion through the inlet port. The rotor portion rotates at a fixed or variable speed and blood components within the rotor portion are separated by centrifugation in accordance with their specific gravities. With blood continuously entering the bowl through the inlet port, the separated various blood components are progressively displaced inwardly from the radially outward portion of the bowl and successively reach a skirt portion which opens radially outwardly and communicates with the outlet port. Blood components exiting through the outlet port are retained and stored, while components remaining in the bowl after collection is complete are then returned to the patient or donor through the outlet port, or deposited in an appropriate container for preservation. The rotor portion comprises a generally frustoconical or cylindrical bowl body and a generally cylindrical core is coaxially disposed therein as the stator portion. Separation by centrifugation is achieved in the space between the core and the bowl body, i.e., a separation chamber. The rotary seal is constructed as a rotary seal assembly including the inlet port and the outlet port and a collection chamber, which is a space for guiding the separated blood components to the outlet port, is formed between the seal and the top of the core. Openings are provided about the core periphery for communication between the separation chamber and the collection chamber. A central opening is formed in the core and a stem for guiding fluid from the inlet port to the lower portion of the bowl is inserted through the central opening.

In addition to the bowls of the above constructions, U.S. Pat. Nos. 4,983,158 and 4,943,273 disclose another types of bowls which are herein referred to as "BM bowl". These bowls include an integral bowl body formed by blow molding and cores of various shapes can be coaxially inserted into the bowl through an aperture formed in one axial end of the bowl body. The bowl of U.S. Pat. No. 4,943,273 features a diverter member, which can be fitted into the bowl by insertion, is provided below the core so that the bowl would be suitable for washing blood cell components collected from a surgical site.

Further, U.S. Pat. No. 5,100,372 discloses an improved core adapted for insertion into a BM bowl, wherein it is taught to provide the core with small size openings for communication between the separation chamber and the collection chamber, so that any blood components remaining on the upper portion of the core can be effectively removed by "splash back".

Moreover, International Publication WO94/08721 pamphlet (PCT/US93/09276) discloses a core for a Grenade bowl for use in blood cell separation or washing, in which the core is provided with a plurality of radially outwardly extending projections for minimizing formation of Coriolis waves which would otherwise cause undesirable turbulence in the separation chamber. Furthermore, a bowl of the BM type for washing or concentrating red blood cells and having only the upper core portion without a body that coaxially extends with the bowl body, is disclosed in International Publication WO89/01792 pamphlet (PCT/US88/02963). Furthermore, U.S. Pat. No. 5,045,048 discloses another type of Latham type bowl. In FIG. 1 of this U.S. Patent, the radially outward periphery of skirt portions 24a and 25a communicating the outlet port is shown closely adjacent to the inner wall of the bowl body. However, no detailed explanation is given.

OBJECT OF THE INVENTION

Conventionally, when blood components are separated using the bowls as described above, plasma and platelets are the components of interest and red blood cells, which eventually remain in the bowl after the separation, are usually returned to the patient or donor. However, there are occasions where red blood cells are separately needed for treatment of diseases, just like plasma and platelets, and a need exists in the medical field for concentrated red blood cells (plasma depleted whole blood). Concentrated red blood cells are about one half of the volume of whole blood while the number of red blood cells and the amount of hemoglobin per unit are the same, thus offering an advantage in that transfusions to patients, in particular to aged and infant patients, are smaller.

Conventional bowls of the types described above suffer from a disadvantage in that, when used for separating concentrated red blood cells from whole blood, the collected concentrated red blood cells are of poor quality. In particular, while BM type bowls are suitable for the purpose of red blood cell separation due to economic reasons, one of the problems associated with the conventional BM type bowls is that white blood cells cannot be separated properly and remain in the concentrated red blood cells. As has been widely known, when concentrated red blood cells contaminated with white blood cells are used for transfusion, there are dangers such as FNHTR (Febril Non-Hemolytic Transfusion Reaction), production of white blood cell antibodies and viral infection carried by white blood cells. Further, in Latham and BM type bowls, even if one attempted to remove white blood cells by continuing the process until red blood cells, the component of the heaviest specific gravity, start to elute from the separation chamber, the problem of contamination with white blood cells is still a plague and, moreover, this approach has been found to give rise to another problem, contamination with free hemoglobin.

Accordingly, it has been conventional to resort to so-called dual bag system or quaternary bag system when it is desired to collect from whole blood concentrated red blood cells substantially free from white blood cells. In the dual bag system, anticoagulated whole blood in a plastic bag is subjected to centrifugation for separating the blood components and the plasma is squeezed out from the bag to obtain concentrated red blood cells, which are then diluted and filtered through a filter for removing white blood cells by adsorption, thereby removing 99% or more of the white blood cells (Shoni Naika 26, 6 (1994)). In the quaternary or four bag system, on the other hand, four bags including a bag containing red blood cell preservant (MAP) are used. By centrifugation after blood collection, blood components are separated as layers in one of the bags in accordance with their specific gravities, and external force is applied to the bag to discharge out from the top portion of the bag to the other bags, in turn, platelet poor plasma, buffy coat, and a top portion of concentrated red blood cells that contains a substantial amount of granulocytes, thereby removing approximately 90% of lymphocytes and approximately 40% of granulocytes (Kiso to Rinsho 29 (12) 3295 (1995)). However, these systems suffer from disadvantages that a high-volume centrifuge apparatus is required and that the operations for separating blood components after centrifugation are complicated.

Accordingly, an object of the present invention is to improve conventional Latham type and BM type bowls such that they would be suitable for collecting concentrated red blood cells depleted of white blood cells.

Another object of the present invention is to improve conventional Latham type and BM type bowls such that separation of blood components such as platelet poor plasma can be achieved more satisfactorily. The improved bowls are provided with novel cores.

As in the case of concentrated red blood cell collection, it is required that white blood cells be removed as much as possible when collection of concentrated platelets is desired. White blood cells are sometimes separated and transfused in aid of immunotherapy. However, these components were not conveniently available in conventional BM type bowls. A further object of the present invention, accordingly, is to provide a BM type bowl which is improved for achieving better separation of components such as platelet concentrate, buffy coat and white blood cells.

A further object of the present invention is to provide a core suitable for such BM type bowl.

DISCLOSURE OF THE INVENTION

A centrifuge bowl for blood processing provided in accordance with the present invention comprises a bowl body adapted for rotation about its axis and having an aperture at one axial end thereof, a rotary seal assembly affixed to the bowl body to cover the aperture and having an inlet port and outlet port in fluid communication with the interior of the bowl body and a core disposed within the bowl body. The core includes a first portion defining a collection chamber that is in fluid communication with the outlet port, and a second portion defining a separation chamber in fluid communication with the inlet port between the core and the inner wall of the bowl body. The core further includes means for defining fluid passages communicating with the collection chamber and the separation chamber and a central opening formed concentric about the axis. The means for defining fluid passages may, in Latham type bowls, for example, be projections or recesses formed around the central opening of the generally frustoconical core, which projections or recesses define fluid passages between the outer surface of the core and the inner surface of the bowl when the core engages the bowl body. Alternatively, such projections or recesses may be formed about the inner surface of the bowl body which engages the core. In the case of cores for use in BM type bowls, the fluid defining means may, for example, be a plurality of openings formed about the periphery of the core, the core which can be inserted into the bowl body.

According to one aspect of the present invention, in a centrifuge bowl of the type described above, the collection chamber is adapted to minimize the holdup volume of blood components therein, the core is provided with a barrier member for preventing flow from the collection chamber into the central opening, and each of the fluid passages has a minimal size for restricting back flow while permitting flow of blood components from the separation chamber to the collection chamber. The term "holdup volume" refers to a maximum possible volume or amount of blood or separated blood components resident in the collection chamber. Such construction enables to prevent rupture of red blood cells in the collection chamber, thereby preventing hemoglobins from flowing out to become free hemoglobins (FHgbs) which are a source of contamination for concentrated red blood cells. Contamination of concentrated red blood cells due to back flow of white blood cells and liberated hemoglobins from the collection chamber to the interior of the bowl can also be prevented.

The outlet port communicates with the collection chamber through a skirt member. The skirt member has a radially outward opening, which is disposed preferably radially inwardly of the fluid passages, and has a small diameter. Typically, the diameter is equal to or less than 33 mm, preferably equal to or less than 28 mm and most preferably equal to or less than 25 mm. The small diameter of the skirt member allows increased shear force between the outer periphery of the skirt member and the opposing surface of the core or bowl body, thereby minimizing rupture of blood cell components in the collection chamber. The outer periphery of the small skirt is preferably disposed closely adjacent to the upper portion, or the first portion of the core or the inner wall of the bowl body, thereby decreasing the shear force and minimizing the holdup volume in the collection chamber. The radial spacing between the skirt periphery, or the skirt opening, and the surface closely adjacent thereto is preferably equal to or less than 2 mm and more preferably equal to or less than 1 mm. The skirt portion usually extends straight in the axial direction. However, so long as a small diameter is maintained, the skirt can assume other shapes such as an axially flared shape.

The fluid passages or openings are 2 or more in number, for example 2 to 8, and are formed equidistantly in the circumferential direction. The total area of the fluid passages or openings is preferably equal to or less than 80 mm$^2$, so as to prevent back flow when blood components are displaced from the separation chamber to the collection chamber. More preferably, the total area is equal to or less than 40 mm$^2$ and most preferably in the range of 20 to 40 mm$^2$.

The barrier member may be a cylindrical hub surrounding the central core opening and extending axially to a position axially closely adjacent to the skirt member. Flow from the collection chamber into the bowl body through the central opening is thereby prevented, thus preventing contamination of concentrated red blood cells with white blood cells and FHgbs. The axial distance between the axial end of the cylindrical hub and the skirt member is typically 2 mm or less and preferably 1 mm or less.

According to another aspect of the present invention, a core for use in a centrifuge bowl of the described character, in particular of the BM type, defines a separation region between the fluid passages or openings and the separation chamber, the axial length of which decreases progressively radially inwardly. For the separation of buffy coat or white blood cells from red blood cells, it is necessary that a phase or layer of white blood cells be grown and led from the outlet port to the exterior of the bowl. Conventional cores for use in BM type bowls assumed a substantially cylindrical shape as a whole, thus no area or region was available for the growth of such white blood cell phase. In the present invention, provision of the separation region having radially inwardly decreasing axial length between the fluid passages or openings of the core and the separation chamber allows easy separation of white blood cells in BM type bowls. Such a separation region enables the separation of platelets and white blood cells, the components which do not differ substantially from each other in specific gravity and thus form a single buffy coat layer (including platelets and white blood cells, i.e., lymphocytes, monocytes and granulocytes) rather than forming separate individual layers. Thus, it becomes possible to collect each of platelet concentrate depleted of white blood cells and white blood cells separately. Preferably, such a separation region is formed between the upper and lower cylindrical core portions, by the lower axial end of the upper cylindrical portion and a radially inward conical taper portion of the lower cylindrical portion.

DESCRIPTION OF PREFERRED EMBODIMENTS

Figure 1:
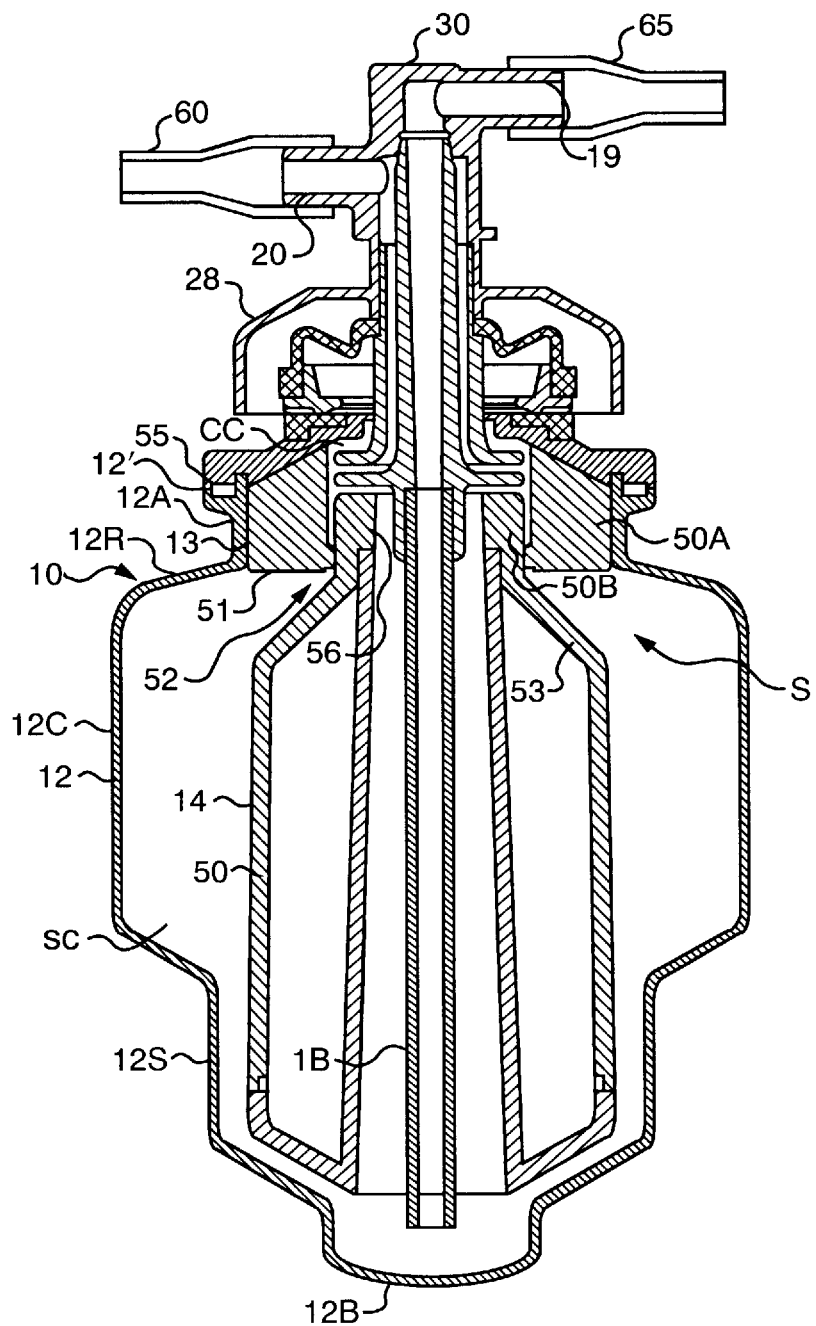
FIG. 1 is an axial sectional view of one embodiment of a BM type centrifuge bowl of the present invention.
Figure 2:
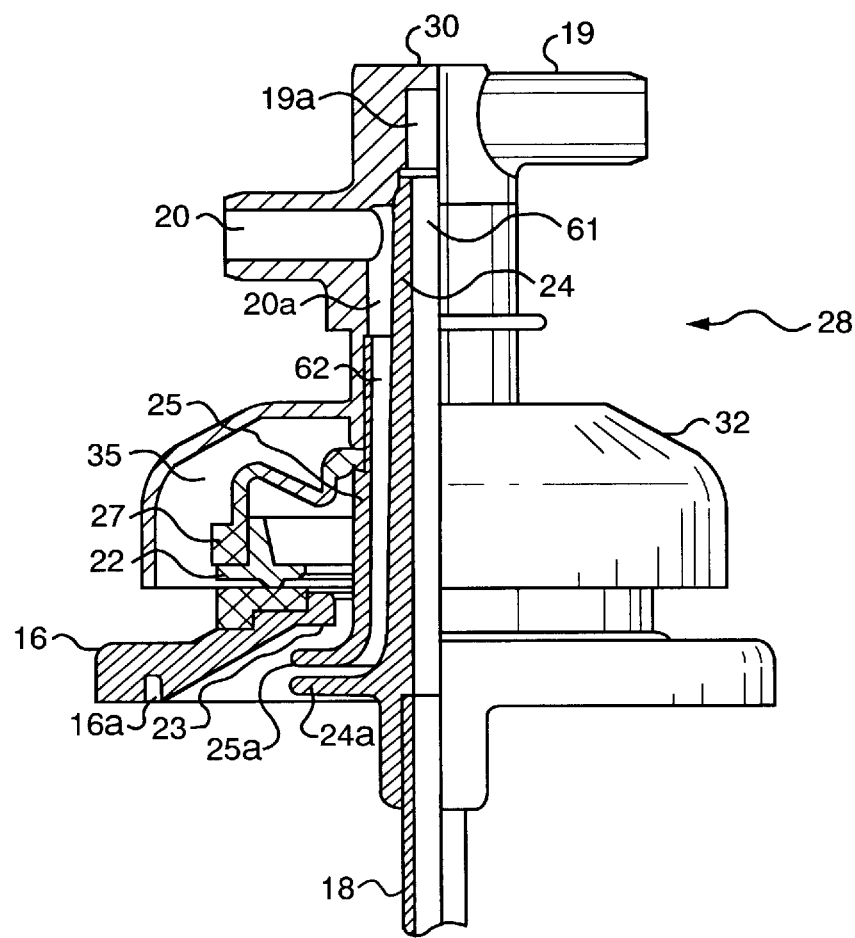
FIG. 2 is a partial cutaway elevational view illustrating the rotary seal assembly used for the centrifuge bowl of FIG. 1.
Figure 3:
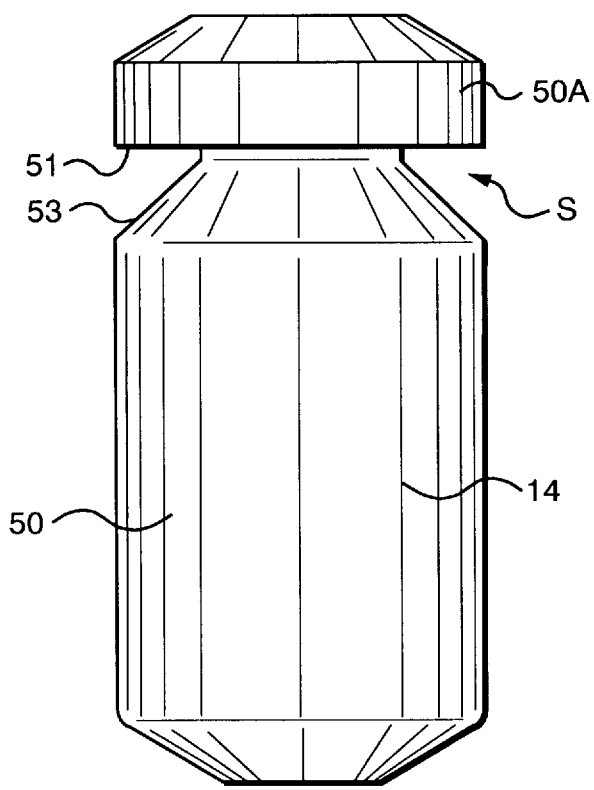
FIG. 3 is a diagrammatic front elevational view of the core of the centrifuge bowl of FIG. 1.

Referring now to FIGS. 1–4, a preferred embodiment according to BM type of the invention will be described. As shown in FIG. 1, a centrifuge bowl of the BM type according to the present invention comprises a disposable centrifuge rotor, or bowl 10, which is used for processing whole blood from a patient or donor, in particular for obtaining concentrated red blood cells substantially free from white blood cells. The bowl 10 comprises a rotary seal assembly, or seal and header assembly, shown generally at 28 (FIG. 2), a seamless one-piece bowl body shown generally at 12 and a core 14 (FIGS. 3 and 4).

The seal and header assembly 28 provides a rotary seal and fluid communication pathway between the interior of the rotatable bowl body 12 and stationary conduits 65 and 60 connected respectively to an inlet port 19 and an outlet port 20. The assembly 28 is comprised of a stationary header, shown generally at 30, an effluent tube 25, a feed tube assembly, shown generally at 24, and a rotary seal, shown generally at 35. The rotary seal 35 comprises a seal ring 22, a flexible member 27 and an outside seal member, or crown 16.

The header 30 is comprised of an integrally formed member having an inlet bore, or inlet port 19, extending radially into an axial passageway 19a. The passageway 19a is coupled to an inner, axially extending bore 61 of feed tube assembly 24 and, in turn, to a feed tube stem 18, thereby forming a non-rotating inlet path for anticoagulated whole blood to enter the interior of centrifuge bowl body 12.

The header 30 also includes an outlet bore, or outlet port 20, which extends radially into a channel 20a extending about feed tube assembly 24 in coaxial relationship. The channel 20a then couples to an outlet passageway 62. An outer shield member 32 is formed on header 30 and extends over rotary seal 35.

Figure 8:
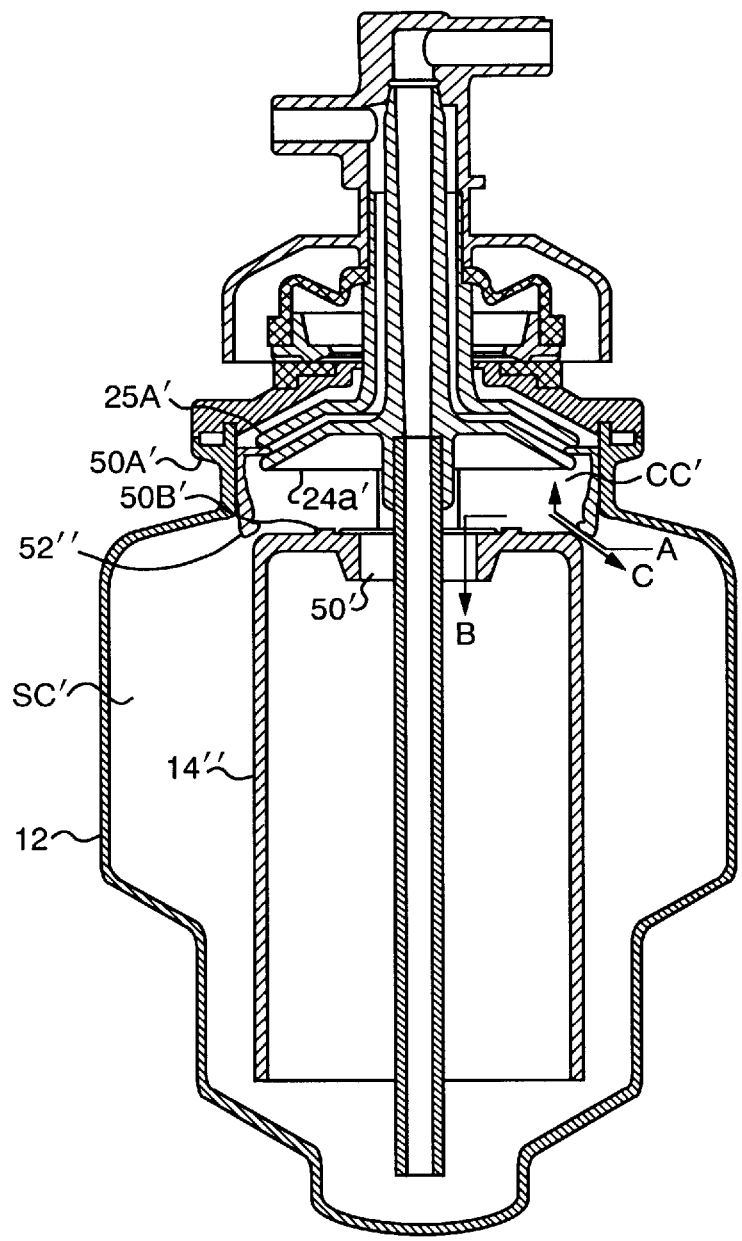
FIG. 8 is an axial sectional view of a prior art BM type centrifuge bowl.

The feed tube assembly 24 is formed with a lower skirt 24a integral therewith and a corresponding, complimentary upper skirt 25a is integrally formed on effluent tube 25, thereby forming a radially outwardly opening skirt member in the collection chamber. The skirt member is of a reduced diameter, relative to prior art skirt member of this type of bowl structure as shown in FIG. 8.

As mentioned above, rotary seal 35 is formed of a flexible member 27, a seal ring 22 and a crown 16. Flexible member 27 is affixed about its outer periphery to the periphery of seal ring 22. Crown 16 includes an axially open groove 16a on its periphery and is provided with a central opening 23, through which effluent tube 25 extends. The inner periphery of flexible member 27 is joined to effluent tube 25.

The header and seal assembly 28, as thus described, is formed and assembled as an individual unit and, after the core 14 has been inserted through an aperture 13 formed in one axial end of bowl body 12 and disposed within the bowl body 12 as shown in FIG. 1, inserted through the opening of bowl body 12 and fixed thereto by appropriate means such as welding or threading.

The bowl body 12 is preferably an integral body adapted to be manufactured by blow molding or injection blow molding and may be formed of a suitable plastic, such as transparent styrene resin or the like.

The bowl body 12 comprises an upper annular portion 12A, an upper radial portion 12R, a cylindrically extending middle portion 12C, a lower stepped portion 12S and a bottom closure portion 12B. A groove 12' corresponding to the groove 16a of crown 16 is formed on annular portion 12A and an O-ring 55 is disposed between the grooves. When the crown 16 is fixed onto bowl body by threading, welding or the like, O-ring 55 is compressed to form a liquid tight seal.

The core 14 is generally cylindrical and is adapted to be disposed within bowl body 12 by insertion through said aperture 13 formed in annular portion 12A of bowl body 12. The core 14 includes a cylindrical portion, or generally cylindrical outer wall 50, extending coaxially with bowl body 12. An upper cylindrical portion, or annular portion 50A of core 14 is adapted to be snugly received in aperture 13 of bowl body 12 when core 14 is inserted into bowl body 12, thereby defining a collection chamber CC between crown 16 and annular portion 50A of core 14 for collecting separated blood components through the skirt member. The annular portion 50A is formed to have a relatively thick wall and the inner wall thereof is disposed radially closely adjacent to the opening of the skirt member, i.e., the periphery of upper and lower skirts 25a and 24a.

Figure 4A:
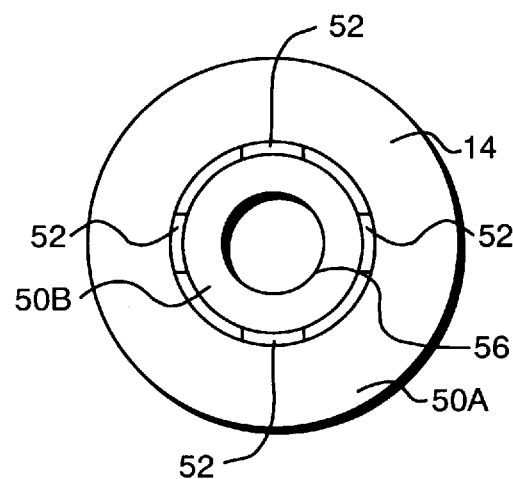
FIG. 4A is a plan view of the core of FIG. 3

Outer wall 50 of core 14 has a diameter approximately equal to that of annular portion 50A and forms a separation chamber SC between outer wall 50 and middle and stepped portions 12C and 12S of bowl body 12. The axial ends of outer wall 50 are tapered and the upper tapered end is joined to the inner periphery of the lower end of annular portion 50A, at which junction four slit-like openings 52 are formed equidistantly at 90 degree intervals about the periphery (FIG. 4A). These openings 52 serve to provide passages for blood components, such as plasma and platelets, separated from whole blood by centrifugation in separation chamber SC in bowl body 12, to flow into collection chamber CC. The tapered distal ends of outer wall 50 are connected with each other through an axially extending cylinder member and feed tube stem 18 extends through the interior of the cylinder member toward the bottom closure portion 12B of bowl body 12.

The lower axial end 51 of annular portion 50A and the upper tapered portion, or radially inward inclination 53 of outer wall 50, define a separation region S, which has radially inwardly progressively decreasing axial length, between openings 52 and separation chamber SC. The upper end of the upper tapered portion of outer wall 50 is integrally joined to a cylindrical hub 50B which extends axially to a position axially closely adjacent to the skirt member and a central opening 56 of core 14 is defined by the hub 50B. The cylindrical hub 50B serves as a barrier that prevents fluid in collection chamber CC from flowing to the interior of bowl body through central opening 56.

For better understanding of the function of the centrifuge bowl 10 shown in FIGS. 1–4, in particular the novel core 14, it may be helpful to refer to the following illustrative two protocols. These processing protocols can be executed utilizing apheresis apparatus available from Haemonetics Corporation of 400 Wood Road, Braintree, Mass. 02184, U.S.A. under the tradenames MCS, MULTI and CCS.

WBC Depleted Concentrated Red Blood Cells Collection Protocol

1. Whole blood is drawn from a patient or donor, anticoagulated and guided into bowl 10 via inlet port 19 through conduit 65. This may be achieved by, for example, driving conduit 65 with a peristaltic pump (not shown). The anticoagulated whole blood is led from inlet port 19 to bottom closure portion 12B of rotatable bowl body 12 through axial passageway 19a, bore 61 and feed tube stem 18. The whole blood is forced radially outwardly from closure portion 12B to separation chamber SC and blood components are separated by the centrifugal force in accordance with the specific gravities. The most heavy fraction, red blood cells, form an outermost cylindrical layer along middle portion 12C of bowl body 12 and plasma layer and buffy coat (platelets and white blood cells) are formed inside thereof in the order of lighter to heavier specific gravities. Granulocytes, which are the most heavy fraction among white blood cells, are however partly distributed about the radially inner side of the layer of concentrated red blood cells. By continuing the withdrawal of whole blood and its introduction into bowl 10 via inlet port 19, the outermost red blood cell layer is grown and the separated blood components enter, in the order of lighter to heavier specific gravities, into collection chamber CC from stepped portion 12S via separation region S and openings 52, flow through the opening of the skirt member, i.e., between upper and lower skirt portions 25a and 24a, to outlet passageway 62, channel 20a and then to outlet port 20, and are led to a blood component storage bag (not shown) through conduit 60.

2. The process is continued until it is detected that a part of the concentrated red blood cells, obtained by centrifugation, has started to flow out from outlet port 20, and rotation of bowl 10 is stopped when such detection is made. The detection can be made automatically by monitoring conduit 60 with an optical sensor.

3. The peristaltic pump driving conduit 65 is then reversed, discharging from inlet port 19 concentrated red blood cells remaining in bowl 10. The discharged concentrated red blood cells can be collected in a bag (not shown) coupled to a line branched from conduit 65 by clamping the line extending from conduit 65 to the patient or donor and by releasing a clamp in the line extending to the collection bag for concentrated red blood cells.

4. After all the concentrated red blood cells in the bowl 10 are discharged, the process can be repeated again. Namely, by releasing the clamp in the line extending between the patient or donor and conduit 65, clamping the line between conduit 65 and the collection bag and forward-rotating the peristaltic pump, the blood separation process can be repeated again and concentrated red blood cells can be collected automatically. The cycle can be repeated as many times as desired.

WBC Depleted Platelet Concentrate Collection Protocol

1. Whole blood drawn from a patient or donor is guided into bowl 10 via inlet port 19 through conduit 65 with the use of a peristaltic pump (not shown) and an anticoagulant is continuously added thereto. The anticoagulated whole blood is led from inlet port 19 to bottom closure portion 12B of rotatable bowl body 12 through axial passageway 19a, bore 61 and feed tube stem 18. As in the case of the WBC depleted concentrated red blood cell collection protocol described above, the whole blood is separated by the centrifugal force into a layer of red blood cells, the radially outermost layer within the bowl, and the inner, buffy coat and plasma layers. By continuing the withdrawal of whole blood, the separated blood components enter, with the plasma layer first, into collection chamber CC via separation region S and openings 52, flow through the opening of the skirt member to outlet passageway 62, channel 20a and then to outlet port 20, and are led to a blood component storage bag (not shown) through conduit 60.

2. When the front end of the buffy coat layer has approached the core openings 52, a surge step is started for separating platelets and white blood cells in the buffy coat layer. Collection of whole blood is stopped and a part of the collected plasma is introduced into the bowl. While the components in the buffy coat having close specific gravities cannot be separated from each other only by centrifugation, if plasma is introduced radially inwardly against the centrifugal force during spinning, platelets, which have a small diameter, are selectively carried out by the plasma. The white blood cells, on the other hand, are retained in the separation region S. The flow rate of plasma introduced can be adjusted, for example, to progressively increase at a predetermined increment. After most of the platelets have been carried out and before white blood cells start to flow out, the plasma introduction is stopped.

3. Uncollected white blood cells and concentrated red blood cells remaining in the bowl are returned to the patient or donor by stopping rotation of the bowl 10 and reversing the peristaltic pump that drives conduit 65. The process may be automatically repeated as desired until a sufficient quantity of platelets has been collected.

Figure 7:
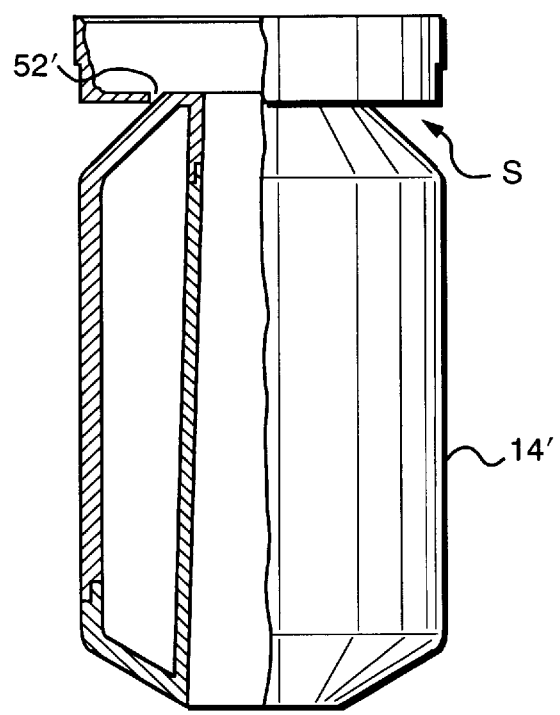
FIG. 7 is a diagrammatic partial cutaway sectional view showing another core of the present invention for use in a BM type centrifuge bowl.

When it is desired to collect concentrated red blood cells with a bowl, it is necessary to clearly form a layer of white blood cells and to expel all of the layer out to the exterior of the bowl. In accordance with the bowl 10 in FIG. 1 of the present invention, separation region S, which has radially inwardly progressively decreasing axial length, is defined by lower axial end 51 of annular portion 50A of core 14 and radially inward inclination 53 in the upper part of outer wall 50, and separated white blood cells are collected, after leaving separation chamber SC and before entering into openings 52, in this separation region S in the form of a layer and thus efficiently expelled through collection chamber CC. In prior art, insertable cores for use in BM type bowls have not been provided with such a separation region S. Such a separation region S is also found to be useful for a conventional structure as shown in FIG. 8 which does not include any of the thick-wall annular portion 50A in the upper core part, the skirt member of a reduced diameter and the cylindrical hub axially extending toward the skirt member. An illustrative example of a core 14' having such useful structure is shown in FIG. 7. Openings 52' in this core 14' can have a slit-like form as in the case of FIG. 4A.

Figure 4B:
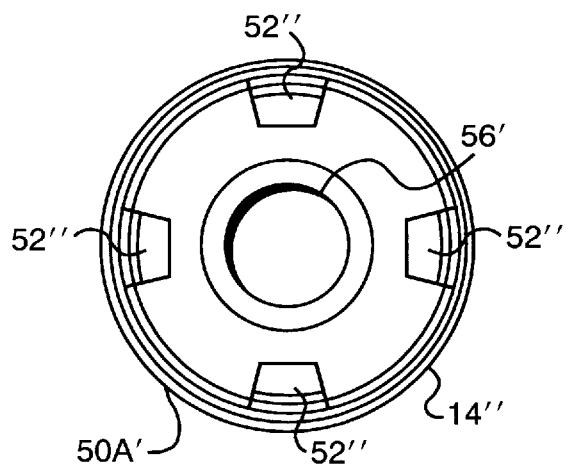
FIG. 4B is a plan view of a prior art centrifuge bowl core of FIG. 8.

Further, when it is desired to collect concentrated red blood cells with a bowl, it is important to prevent contamination of the concentrated red blood cells remaining in the bowl by white blood cells and free hemoglobins. In a bowl comprising a core 14" of the conventional structure as shown in FIGS. 4B and 8, blood components are radially displaced from outward to inward in the order of lighter to heavier specific gravities, enter collection chamber CC' from separation chamber SC' through openings 52" and guided to the outlet port via the opening in the skirt member (arrow A). However, collection chamber CC' is not constructed to control the behavior of fluid therein. Accordingly, the white blood cells entered into collection chamber CC' through openings 52" are allowed to return to the interior of bowl body 12 from central opening 56' while residing in collection chamber CC' (arrow B), thereby contaminating the concentrated red blood cells in the bowl. The area of openings 52" is relatively large and this allows back flow from collection chamber CC' to separation chamber SC' when the components flow into collection chamber CC' from separation chamber SC' , also resulting in contamination of the concentrated red blood cells in the bowl with white blood cells.

In addition, when red blood cells are partly expelled from the bowl for complete expulsion of white blood cells and granulocytes from the bowl, the red blood cells residing in collection chamber CC', before being guided to the outlet port from the skirt member 24a', 25a', are ruptured between the relatively large-diameter skirt member and the upper core wall spinning therearound. The hemoglobins are thereby released from the cells and allowed to return to the interior of the bowl along the arrows B and/or C, thereby causing contamination.

In accordance with the present invention, the fluid-behavior uncontrolled collection chamber of the prior art is modified by the thick-wall annular portion 50A closely disposed adjacent to the opening of the skirt member so as to minimize the holdup volume of blood components within the collection chamber. In addition, the cylindrical hub 50B axially extending to a position closely adjacent to the skirt member prevents return of flow from collection chamber CC into central opening 56. The skirt member per se is of a reduced diameter for preventing rupture of blood cells and the openings 52 are of a size that prevents back flow while permitting flow from separation chamber SC and separation region S into collection chamber CC. The flow of separated blood components tending to return to the interior of the bowl from collection chamber CC through central opening 56 and/or openings 52 is thus inhibited, and contamination by free hemoglobins is also prevented because of the minimized holdup volume.

In addition, with regard to the barrier formed by the cylindrical hub 50B, when the front end of blood components displaced radially inwardly within the collection chamber reaches the skirt opening, air cannot escape from within the bowl and thus the collection chamber will not be overfilled with blood components. Further, blood components resident in the collection chamber are subjected to centrifugal force. Therefore, blood components in the collection chamber will not backflow from the central opening into the bowl through the axial spacing between the top of hub 50B and the bottom of lower skirt 24a, provided that the top of hub 50B is sufficiently close to the bottom of lower skirt 24a and the diameter of central opening 56 is sufficiently small. As the top end of hub 50B axially faces the lower skirt 24a, the diameter of hub 50B is equal to or smaller than the skirt diameter and the diameter of central opening defined by the hub is sufficiently small.

Figure 5:
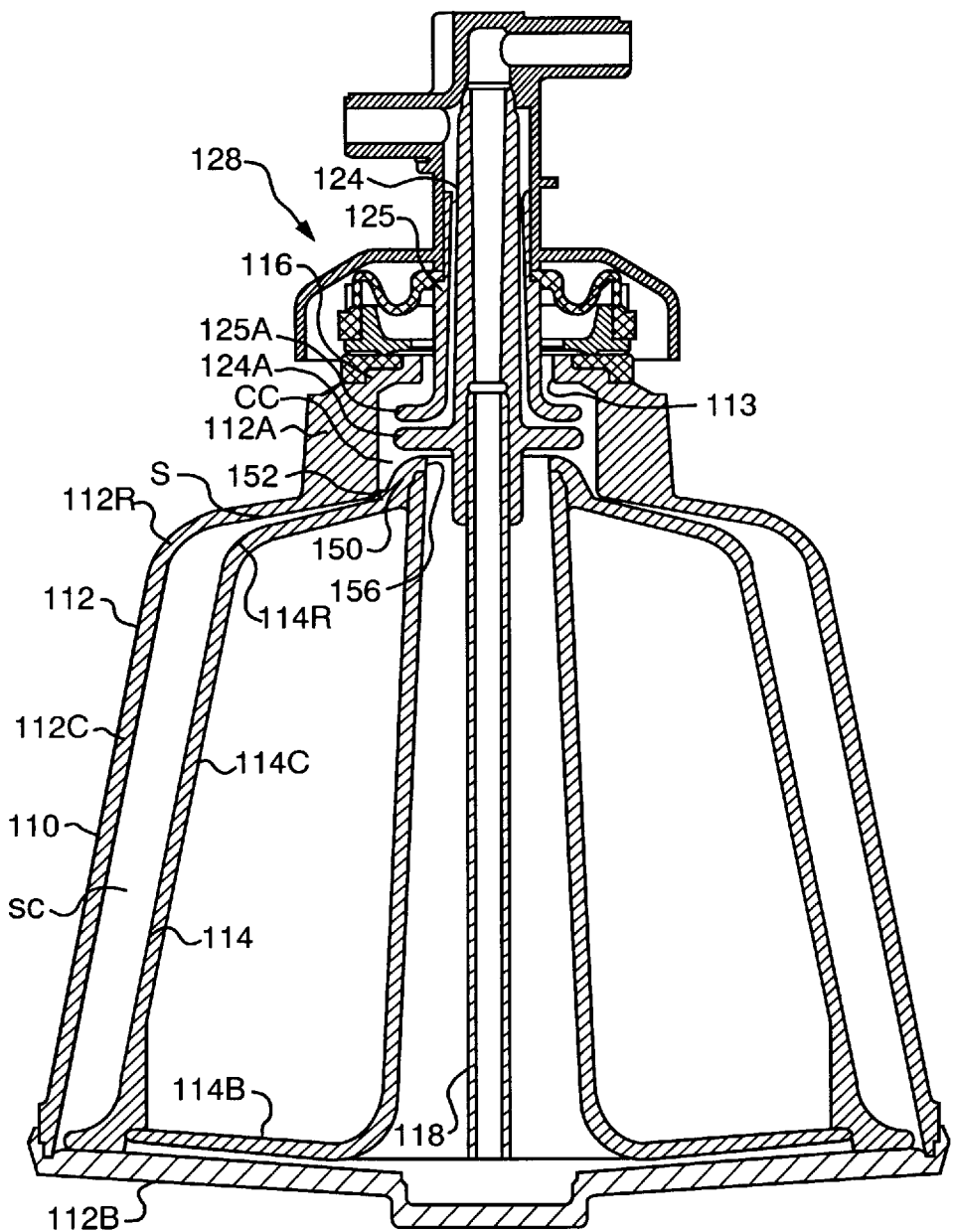
FIG. 5 is an axial sectional view of one embodiment of a Latham type centrifuge bowl of the present invention.

Turning now to FIGS. 5 and 6, a preferred embodiment according to Latham type of the invention will be described. As shown in FIG. 5, the centrifuge bowl of Latham type also comprises a disposable centrifuge rotor, or bowl 110, which has an aperture 113 at one end and comprises a rotary seal assembly 128, a bowl body 112 and a core 114. The rotary seal assembly 128 is substantially of the same construction as the rotary seal assembly 28 described above with reference to FIG. 2, and thus is not detailed herein to avoid redundancy. It should be noted that in this case, too, a radially outwardly opening skirt member having a small diameter is provided by a lower skirt 124a formed integral with feed tube assembly 124 and a corresponding, complimentary upper skirt 125a integrally formed on effluent tube 125.

The bowl body 112 may be formed of a suitable plastic material such as transparent styrene resin or the like and comprises an upper annular portion 112A, an upper radial portion 112R, a middle portion 112C conically extending down from the radial portion 112R, and a separate, disc-like bottom portion 112B. The crown 116 of rotary seal assembly 128 is affixed onto annular portion 112A by threading, welding or the like.

The core 114 disposed within bowl body 112 has a profile corresponding to the bowl body 112 and comprises a radial portion 114R extending along radial portion 112R, a middle portion 114C extending conically down from the radial portion 114R and a bottom portion 114B corresponding to bottom portion 112B. A cylindrical hub 150 that extends axially to a position axially closely adjacent to the skirt portion is formed around the periphery of a central opening 156. Annular portion 112A of bowl body 112, the portion which defines a collection chamber CC for collecting separated blood components through the skirt member, is formed to have a relatively thick wall as shown, the radially inner wall of which is disposed radially closely adjacent to the opening of the skirt member, i.e., the periphery of upper and lower skirts 125a and 124a. The collection chamber CC is thus constructed to minimize the holdup volume of blood components.

Figure 6A:
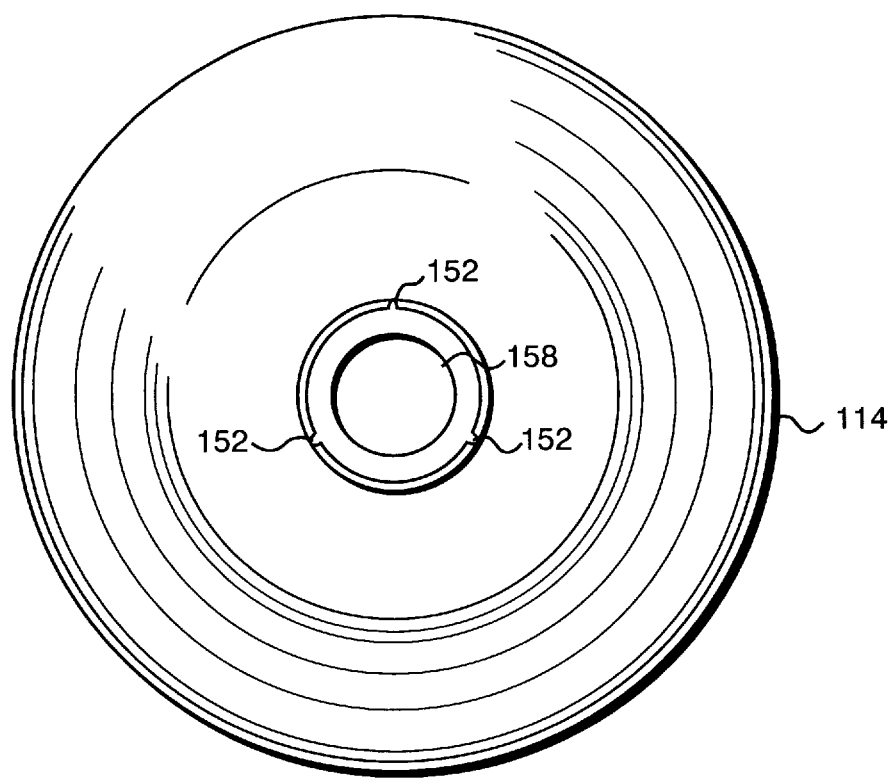
FIGS. 6A and 6B are diagrammatic plan and front elevational views, respectively, of the core of the centrifuge bowl of FIG. 5.
Figure 6B:
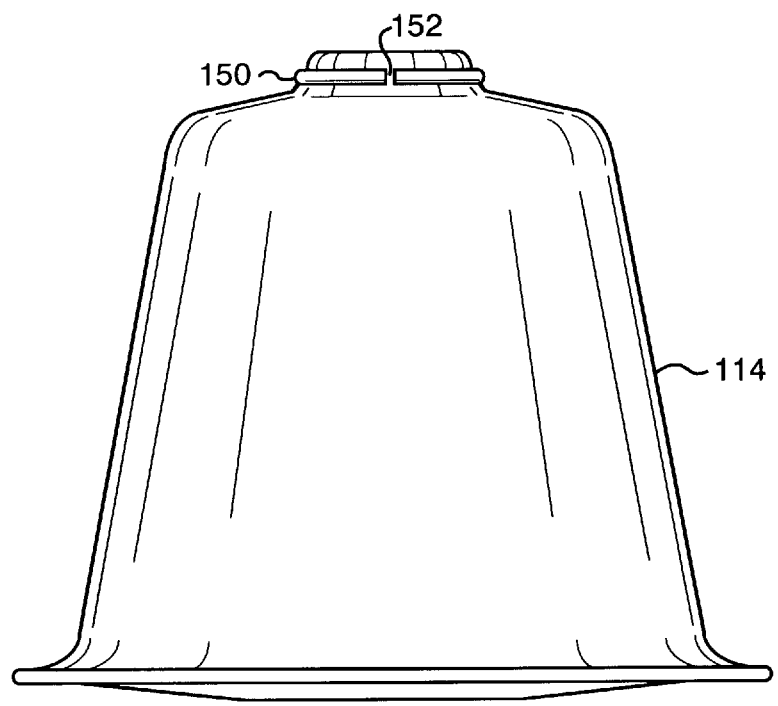

A separation chamber SC is defined between middle portion 114C of core 114 and middle portion 112C of bowl body 112. About the periphery of the lower end of hub 150 abutting the lower inner periphery of annular portion 112A of bowl body 112, three recesses 152 are formed equidistantly at 120 degree intervals as shown in FIGS. 6A and 6B. These recesses 152 serve to provide passages for blood components separated within bowl body 112, such as plasma and platelets, between separation chamber SC and collection chamber CC. The lower end of cylindrical hub 150 and the inner periphery of the disc-like bottom portion 114B are connected with each other through an axially extending cylinder member, and feed tube stem 118 extends through the interior of the cylinder member toward the bottom portion 112B of bowl body 112. Instead of recesses 152, recesses can be formed about the lower inner periphery of annular portion 112A of bowl body 112 to provide the fluid passages.

Figure 9:
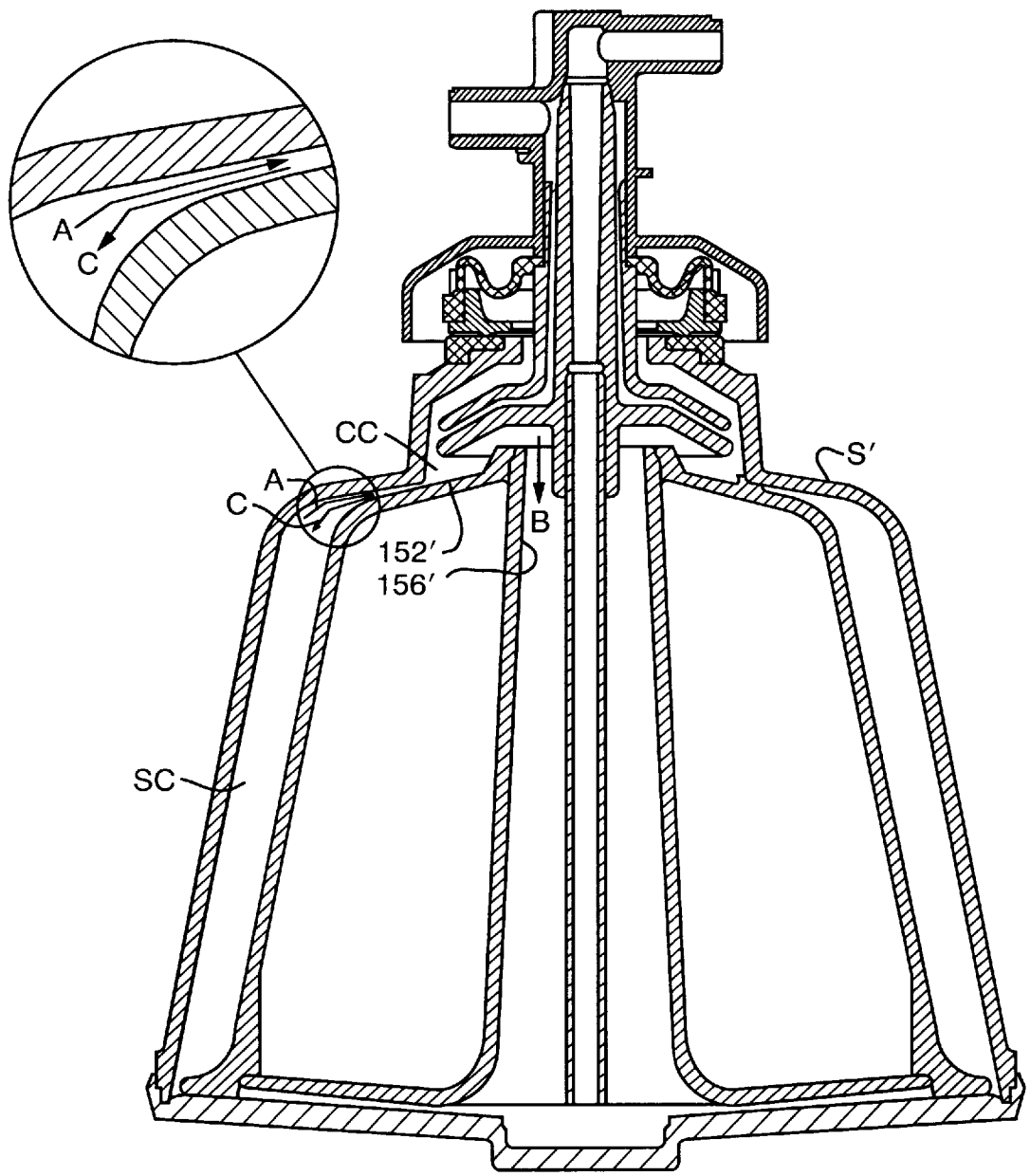
FIG. 9 is an axial sectional view of a prior art Latham type centrifuge bowl.

A separation region S, which has radially inwardly progressively decreasing axial length, is defined between radial portion 112R of bowl body and radial portion 114R of core 114. While such a separation region S has been conventional in Latham type bowls as shown in FIG. 9, the region S is radially extended in accordance with the present invention, thereby enabling better separation of blood components, in particular buffy coat and white blood cells.

Figure 10:
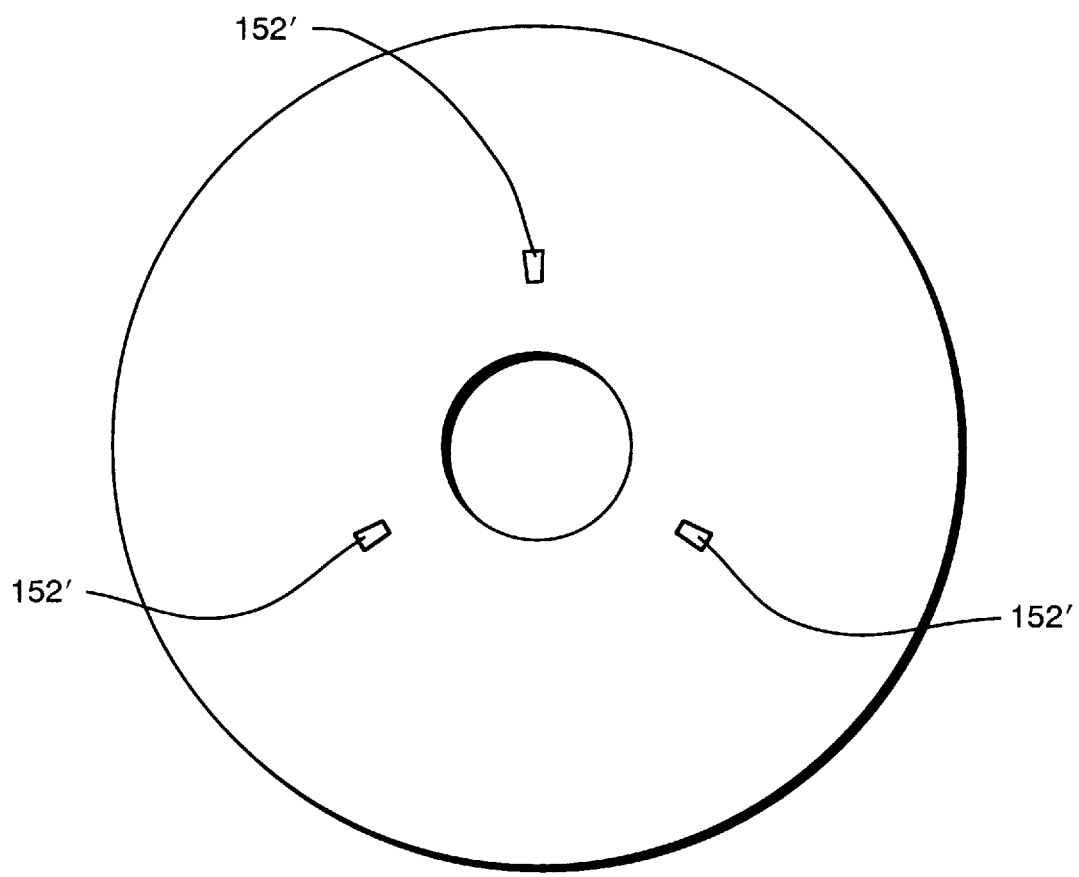
FIG. 10 is a plan view of a core for use in the centrifuge bowl of FIG. 9.

The centrifuge bowl 110 shown in FIGS. 5 and 6 may be used in accordance with processing protocols similar to the protocol illustratively explained above in connection with the embodiment of FIGS. 1–4, employing the same apheresis apparatus. And the same advantages as described above can be obtained in this case as well. Namely, in a bowl with a core of prior art structure as shown in FIGS. 9 and 10, concentrated red blood cells in the bowl are contaminated by white blood cells due to return of flow from collection chamber CC' to the interior of bowl body 112 through central opening 156' (arrow B) and back flow through relatively large-area openings 152' (arrow C), when blood components are guided along the arrow A from separation chamber SC to collection chamber CC' through openings 152'. In addition, when red blood cells are partly expelled from the bowl for complete expulsion of white blood cells and granulocytes from the bowl, the red blood cells residing in collection chamber CC', before being guided to the outlet port from the skirt member, are ruptured between the relatively large-diameter skirt member and the upper annular wall of bowl body spinning therearound, thus releasing hemoglobins which are allowed to return to the interior of the bowl along the arrows B and/or C to cause contamination.

In contrast, in accordance with the present invention, the collection chamber CC is constructed to minimize the holdup volume of blood components therein, with the use of the thick-wall annular portion 112A disposed closely adjacent to the opening of the skirt member. The cylindrical hub 150 that extends axially to a position closely adjacent to the skirt member prevents return of flow from collection chamber CC into central opening 156. The skirt member per se is of a reduced diameter for preventing rupture of blood cells and the openings 152 are of a size that prevents back flow while permitting flow from separation chamber SC and separation region S into collection chamber CC. The flow of separated blood components tending to return to the interior of the bowl from collection chamber CC through central opening 156 and/or openings 152 is thus inhibited, and contamination by free hemoglobins is also prevented owing to the minimized holdup volume. In this case, the diameter of hub 150 is equal to or less than the skirt diameter and the diameter of central opening 156 is thereby sufficiently small, thus preventing, together with the minimal axial spacing between the top of hub 150 and the bottom of lower skirt 124a, backflow from collection chamber CC.

EXAMPLES

Example 1

A centrifuge bowl of the construction shown in FIG. 1 was prepared. The bowl body 12 and seal and header assembly 28 had the same structure as those available from Haemonetics Corporation of 400 Wood Road, Braintree, Mass. 02184, U.S.A. under the tradenames Haemonetics Multicomponent Set (Product #751, #803) and Haemonetics Disposable Plasma Collection Set (Special) (Product #525, #525J), except that the skirt member of the seal and header assembly, i.e., upper skirt 25a and lower skirt 24a had a smaller diameter of about 25 mm. The axial length of core 14 was about 100 mm and included the upper cylindrical portion, annular portion 50A, a cylindrical outer wall 50 having radially inward inclinations at its axial ends and a cylindrical hub 50B axially extending from the junction between annular portion 50A and outer wall 50. Annular portion 50A was formed with the outer diameter of about 48 mm and the inner diameter of about 27 mm and the diameter of outer wall 50 was about 47 mm. The angle contained between the generally radially extending lower end 51 of annular portion 50A and the upper inclination of outer wall 50 was about 45 degrees. The cylindrical hub 50B has the outer diameter of about 25 mm and the inner diameter, or the central opening, of about 14 mm. The diameter of the lower core opening opposite the central opening was about 20 mm. Four slit-like openings 52 of about 0.7 mm in the radial direction were provided equidistantly in the circumferential direction, the total area of opening was about 28 mm$^2$. The radial distance between the skirt member and the inner wall of annular portion 50A was about 1 mm and the axial distance between the lower surface of lower skirt 24a and the upper end of cylindrical hub 50B was about 1 mm.

The above centrifuge bowl was placed on an apheresis machine available from Haemonetics Corporation under the tradename Haemonetics Multicomponent System (MCS3p). Whole blood was drawn from 23 donors and concentrated red blood cells were separated by centrifugation in one cycle, in accordance with the WBC depleted concentrated red blood cells collection protocol. The centrifugation was continued until red blood cells partly flew out from outlet port 20. The rotation speed was 7000 rpm for 13 donors, 6000 rpm for 4 donors and 5000 rpm for 6 donors. Removal rates of white blood cells, granulocytes and lymphocytes, yield of red blood cells, and amount of free hemoglobins (FHgbs) per unit volume were measured in the collected concentrated red blood cells and averaged. The results are shown in Table 1.

Comparative Example 1

A centrifuge bowl having the structure shown in FIG. 8 was prepared. The bowl was available from Haemonetics Corporation under the tradenames Haemonetics Multicomponent Set (Product #751, #803) and Haemonetics Disposable Plasma Collection Set (Special) (Product #525, #525J). The diameter of the skirt member of this bowl was about 41 mm, the total area of four openings 52' of core 14" was about 150 mm², the radial distance between the skirt member and the inner wall of upper core annular portion 50A' was about 3 mm and the axial distance between the lowermost end of the skirt member and the disc-like portion 50B' of the core was about 9 mm. With this bowl, concentrated red blood cells were obtained from 8 donors in the same manner as in Example 1, and the rotation speed was 7000 rpm for all of the donors. The results are also shown in Table 1.

TABLE 1

|  | Removal Rates (%) | | | RBCs yield (%) | FHgbs (mg/dl) |
| --- | --- | --- | --- | --- | --- |
|  | WBCs | Granulocytes | Lymphocytes |  |  |
| Example 1 | 65.1 | 42.6 | 95.6 | 83.7 | 12.0 |
| Comparative Example 1 | 33.6 | 24.5 | 49.2 | 86.9 | 67.1 |

Example 2

A centrifuge bowl of the construction shown in FIG. 5 was prepared. The centrifuge bowl differed from the centrifuge bowl of FIG. 9 available from Haemonetics Corporation under the tradenames Haemonetics Multicomponent Set (Product #890J, #895J, #870) and Haemonetics Disposable ESP Set (Product #790, #795J) in the following points: In the former, the skirt member, i.e., upper and lower skirts 125a and 124a, was of a reduced diameter of about 30 mm, the upper annular portion 112A of bowl body 112 had an inner diameter of about 32 mm and the radial spacing between the skirt member and the opposing inner wall of annular portion 112A was about 1 mm. The cylindrical hub 150 extended axially to define about 1 mm of axial distance between its upper end and the lower surface of the lower skirt 124a. In addition, three recesses 152 were formed as shown in FIG. 6A about the periphery of the lower end of hub 150 abutting the lower inner periphery of annular portion 112A of bowl body 112, and fluid passages having the area of about 21 mm² in total were defined thereby. In contrast, in the latter, currently available bowl, the radial spacing between the skirt member and the inner wall of annular bowl body portion was about 2 mm, the axial distance between the skirt member and the upper core end was about 7 mm and the total area of fluid passages was about 97 mm².

The centrifuge bowl of the FIG. 5 construction was placed on an apheresis machine available from Haemonetics Corporation under the tradename Haemonetics Multicomponent System (MCS3p). Whole blood was drawn from 11 donors and concentrated red blood cells were separated and evaluated in the same manner as in Example 1. The centrifugation was conducted at 6000 rpm for all of the donors. The results are shown in Table 2.

Comparative Example 2

A centrifuge bowl having the structure shown in FIG. 9 was used and concentrated red blood cells were obtained from 10 donors in the same manner as of Example 2. The centrifugation was conducted at 6000 rpm for all of the donors. The results are also shown in Table 2.

TABLE 2

|  | Removal Rates (%) | | | RBCs yield (%) | FHgbs (mg/dl) |
| --- | --- | --- | --- | --- | --- |
|  | WBCs | Granulocytes | Lymphocytes |  |  |
| Example 2 | 80.8 | 69.1 | 97.2 | 73.2 | 15.5 |
| Comparative Example 2 | 71.2 | 44.3 | 98.1 | 80.0 | 48.2 |

Example 3

A centrifuge bowl of the same type as used in Example 1 was placed on an apheresis machine available from Haemonetics Corporation under the tradename Haemonetics Multicomponent System (MCS3p). Platelet concentrate was collected in one cycle by centrifugation at 6000 rpm in accordance with the WBC depleted platelet concentrate collection protocol. Yields were measured in the separated platelet concentrate and the results are shown in Table 3.

Comparative Example 3

A centrifuge bowl of the same type as used in Comparative Example 1 was employed and platelet concentrate was separated in the same manner as in Example 3, except that the bowl was rotated at 7000 rpm. The results are also shown in Table 3.

TABLE 3

|  | Platelet Concentrate | Yield/Bag | | Blood Measurements Before Collection (per µl) | |
| --- | --- | --- | --- | --- | --- |
|  |  | WBCs | Volume (ml) | Platelets | WBCs |
| Example 3 | $1.6*10^{10}$ | $2.5*10^{6}$ | 61 | $3.6*10^{5}$ | $8.2*10^{3}$ |
| Comparative Example 3 | $1.5*10^{10}$ | $9.4*10^{7}$ | 111 | $2.1*10^{5}$ | $4.3*10^{3}$ |

As explained above, novel centrifuge bowls have been provided, which are suitable for obtaining in an apheresis machine concentrated red blood cells depleted of white blood cells. The bowls are also useful in separating blood components such as platelet poor plasma, platelet concentrate depleted of white blood cells, buffy coat and white blood cells more efficiently.

We claim:

1. A centrifuge bowl for processing blood by centrifugation comprising:

a bowl body having an interior and an inner wall, the bowl being configured for rotation about its axis and having an aperture at an axial end thereof;

a rotary seal assembly affixed to said bowl body to cover said aperture and having an inlet port and outlet port in fluid communication with the interior of said bowl body; and a core disposed within said bowl body and having a first portion defining a collection chamber in fluid communication with said outlet port, a second portion defining a separation chamber in fluid communication with said inlet port between the core and the inner wall of said bowl body, means for defining fluid passages communicating said collection chamber and said separation chamber, and a central opening formed concentrically about said axis, characterized in that:

said collection chamber is configured to minimize the holdup volume of blood components therein;

said core is provided with a barrier member for preventing flow from said collection chamber into said central opening; and each of said fluid passages have a minimal size for restricting back flow while permitting flow of blood components from said separation chamber to said collection chamber.

2. The centrifuge bowl as in claim 1, wherein said outlet port communicates with said collection chamber through a skirt member which includes a radially outward opening disposed radially inwardly of said fluid passages, said skirt member having a diameter.

3. The centrifuge bowl as in claim 2, wherein said diameter is equal to or less than 33 mm.

4. The centrifuge bowl as in claim 3, wherein said diameter is equal to or less than 28 mm.

5. The centrifuge bowl as in claim 2, wherein at least one of said first portion and said inner wall of said bowl body is disposed closely adjacent to said skirt member for reducing the volume of said collection chamber, thereby minimizing holdup volume.

6. The centrifuge bowl as in claim 2, wherein said barrier member is a cylindrical hub which extends axially from said second portion to an axial ends said axial end having a position axially closely adjacent to said skirt member.

7. The centrifuge bowl as in claim 6, wherein an axial spacing between said axial end of said cylindrical hub and said skirt portion is equal to or less than 2 mm.

8. The centrifuge bowl as in claim 7, wherein said axial spacing is equal to or less than 1 mm.

9. The centrifuge bowl as in claim 1, wherein said core defines a separation region between said fluid passages and said separation chamber, said separation region having an axial length that decreases radially inwardly.

10. The centrifuge bowl as in claim 1, wherein said fluid passages have a total area equal to or less than 80 mm$^2$.

11. The centrifuge bowl as in claim 10, wherein said total area is equal to or less than 50 mm$^2$.

12. The centrifuge bowl as in claim 1, wherein said fluid passages are 2 or more in number and are circumferentially equidistant.

13. A centrifuge bowl for processing blood by centrifugation comprising:

a bowl body configured for rotation about its axis and having an aperture at an axial end thereof;

a rotary seal assembly affixed to said bowl body to cover said aperture and having an inlet port and outlet port in fluid communication with the interior of said bowl body; and a core inserted into said bowl body through said aperture and having (a) a first cylindrical portion received in said aperture and including a radial inner wall, said first cylindrical portion defining a collection chamber in fluid communication with said outlet port, (b) a second cylindrical portion axially extending from a junction with said first cylindrical portion and defining a separation chamber in fluid communication with said inlet port between the core and the inner wall of said bowl body, (c) openings formed between said first cylindrical portion and said second cylindrical portion and communicating said collection chamber and said separation chamber, and (d) a central opening formed concentrically about said axis, characterized in that:

said outlet port communicates with said collection chamber through a skirt member which is of a reduced diameter and including a radially outward opening;

the radial inner wall of said first cylindrical portion is disposed radially closely adjacent to said opening of said skirt member;

said second cylindrical portion is provided with a cylindrical hub which extends axially from the junction between said first and second portions to a position axially closely adjacent to said skirt member, said cylindrical hub defining said central opening; and each of said openings have a minimal size for restricting back flow while permitting flow of blood components from said separation chamber to said collection chamber.

14. The centrifuge bowl as in claim 13, wherein said first cylindrical portion and said second cylindrical portion define a separation region between said openings and said separation chamber, said separation region having an axial length that decreases radially inwardly.

15. The centrifuge bowl as in claim 14, wherein said separation region is defined between said first cylindrical portion and said second cylindrical portion by an axial end of said first cylindrical portion and a radially inwardly deflecting portion of said second cylindrical portion.

16. A core for use in a centrifuge bowl for processing blood by centrifugation, said centrifuge bowl comprising a bowl body having an interior and an inner wall, the bowl being configured for rotation about its axis and having an aperture at an axial end thereof and a rotary seal assembly affixed to said bowl body to cover said aperture and having an inlet port and outlet port in fluid communication with the interior of said bowl body, said core being insertable into said bowl body through said aperture and having (a) a first cylindrical portion to be received in said aperture and having a radial inner wall, the first cylindrical portion defining a collection chamber in fluid communication with said outlet port, (b) a second cylindrical portion axially extending from a junction with said first cylindrical portion for defining a separation chamber in fluid communication with said inlet port between the core and the inner wall of said bowl body, (c) openings formed between said first cylindrical portion and said second cylindrical portion for communicating said collection chamber and said separation chamber, and (d) a central opening formed concentrically about said axis, characterized in that:

said first cylindrical portion is configured to minimize holdup volume of blood components in said collection chamber;

said second cylindrical portion is provided with a cylindrical hub which extends axially from the junction between said first and second cylindrical portions for preventing flow from said collection chamber into said central opening, said cylindrical hub defining said central opening; and each of said openings have a minimal size for restricting back flow while permitting flow of blood components from said separation chamber to said collection chamber.

17. The core as in claim 16, wherein said first cylindrical portion and said second cylindrical portion define together a separation region between said openings and said separation chamber, said separation region having an axial length that decreases radially inwardly.

18. The core as in claim 17, wherein said separation region is defined between said first cylindrical portion and said second cylindrical portion by an axial end of said first cylindrical portion and a radially inwardly deflecting portion of said second cylindrical portion.

19. The core as in claim 16, wherein said openings have a total area equal to or less than 80 mm$^2$.

20. The core as in claim 19, wherein said total area is equal to or less than 50 mm$^2$.

21. The core as in claim 16, wherein said openings are 2 or more in number and are circumferentially equidistant.

22. A centrifuge bowl for processing blood by centrifugation comprising:

a bowl body having first and second axial ends, an interior and an inner wall, the bowl being configured for rotation about its axis and having an aperture at one of the axial ends thereof, said bowl body conically flaring from one of the axial ends to the other axial end;

a rotary seal assembly affixed to said bowl body to cover said aperture and having an inlet port and outlet port in fluid communication with the interior of said bowl body; and a core disposed within said bowl body and having (a) a first portion extending generally radially for defining a collection chamber in fluid communication with said outlet port, (b) a second portion extending from a junction with said first portion generally radially and then conically for defining a separation chamber in fluid communication with said inlet port between the core and the inner wall of said bowl body, and (c) a central opening formed concentrically about said axis, means provided in at least one of said core and said bowl body for defining fluid passages communicating said collection chamber and said separation chamber, characterized in that:

said outlet port communicates with said collection chamber through a skirt member including a radially outward opening disposed radially inwardly of said fluid passages;

said aperture of said bowl body is formed cylindrically and has a radial inner wall disposed radially closely adjacent to said opening of said skirt member;

said first portion is provided with a cylindrical hub which extends axially from the junction between said first and second portions to a position axially closely adjacent to said skirt member;

each of said fluid passages have a minimal size for restricting back flow while permitting flow of blood components from said separation chamber to said collection chamber; and said section of said second portion extending generally radially from said first portion is configured to define with the inner wall of said bowl body a separation region between said fluid passages and said separation chamber, the separation region having an axial length that decreases radially inwardly.

23. The centrifuge bowl as in claim 22, wherein said skirt member has a diameter equal to or less than 33 mm.

24. A centrifuge bowl for processing blood by centrifugation comprising:

a bowl body having an interior and an inner wall, the bowl being configured for rotation about its axis and having an aperture at an axial end thereof;

a rotary seal assembly affixed to said bowl body to cover said aperture and having an inlet port and outlet port in fluid communication with the interior of said bowl body; and a core inserted into said bowl body through said aperture and having (a) a first cylindrical portion received in said aperture and defining a collection chamber in fluid communication with said outlet port through a skirt member having a radially outward opening, (b) a second cylindrical portion axially extending from said first cylindrical portion and defining a separation chamber in fluid communication with said inlet port between the core and the inner wall of said bowl body, (c) openings formed between said first cylindrical portion and said second cylindrical portion and communicating said collection chamber and said separation chamber, and (d) a central opening formed concentrically about said axis, said first cylindrical portion and said second cylindrical portion defining a separation region between said openings and said separation chamber, said separation region having an axial length that decreases radially inwardly.

25. The centrifuge bowl as in claim 24, wherein said separation region is defined between said first cylindrical portion and said second cylindrical portion by an axial end of said first cylindrical portion and a radially inwardly deflecting portion of said second cylindrical portion.

26. A core for use in a centrifuge bowl for processing blood by centrifugation, said centrifuge bowl comprising a bowl body having an interior and an inner wall, the bowl being configured for rotation about its axis and having an aperture at an axial end thereof and a rotary seal assembly affixed to said bowl body to cover said aperture and having an inlet port and outlet port in fluid communication with the interior of said bowl body, said core being insertable into said bowl body through said aperture and having (a) a first cylindrical portion to be received in said aperture for defining a collection chamber in fluid communication with said outlet port, (b) a second cylindrical portion axially extending from said first cylindrical portion for defining a separation chamber in fluid communication with said inlet port between the core and the inner wall of said bowl body, (c) openings formed between said first cylindrical portion and said second cylindrical portion for communicating said collection chamber and said separation chamber, and (d) a central opening formed concentrically about said axis, said first cylindrical portions and said second cylindrical portion defining a separation region between said openings and said separation chamber, said separation region having an axial length that decreases radially inwardly.

27. The core as in claim 26, wherein said separation region is defined between said first cylindrical portion and said second cylindrical portion by an axial end of said first cylindrical portion and a radially inwardly deflecting portion of said second cylindrical portion.

* * * * *